(12) United States Patent
Harvey

(10) Patent No.: US 8,809,042 B1
(45) Date of Patent: Aug. 19, 2014

(54) PLUG FLOW REACTOR PROCESS FOR ANAEROBIC CELLULOSIC ETHANOL

(75) Inventor: Steven P. Harvey, Lutherville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 558 days.

(21) Appl. No.: 13/276,658

(22) Filed: Oct. 19, 2011

Related U.S. Application Data

(63) Continuation-in-part of application No. 11/926,213, filed on Oct. 29, 2007.

(51) Int. Cl.
*C12M 1/12* (2006.01)
*C12P 7/06* (2006.01)
*C12M 1/00* (2006.01)

(52) U.S. Cl.
CPC . *C12P 7/06* (2013.01); *C12M 29/04* (2013.01)
USPC .................. 435/297.1; 435/290.2; 435/293.1; 435/162

(58) Field of Classification Search
CPC ...... C12M 29/04; C12M 23/34; C12M 25/02; C12M 23/08; C12M 23/24; C12M 21/04; C05F 17/02; C05F 17/0235; C05F 17/0258; C05F 17/0205
USPC ........ 435/162, 293.1, 294.1, 813, 819, 397.1, 435/290.2
See application file for complete search history.

(56) References Cited

U.S. PATENT DOCUMENTS 3,234,026 A * 2/1966 Coutts ............................ 426/16
2009/0130704 A1 * 5/2009 Gyure ............................. 435/41

* cited by examiner

*Primary Examiner* — Michael Hobbs
(74) *Attorney, Agent, or Firm* — Ulysses John Biffoni

(57) ABSTRACT

The present invention is generally related to systems and methods to permit the growth of anaerobic, ethanol-producing bacteria using pretreated biomass such as cellulose in a manner to facilitate the efficient conversion of cellulose to ethanol.

19 Claims, 1 Drawing Sheet

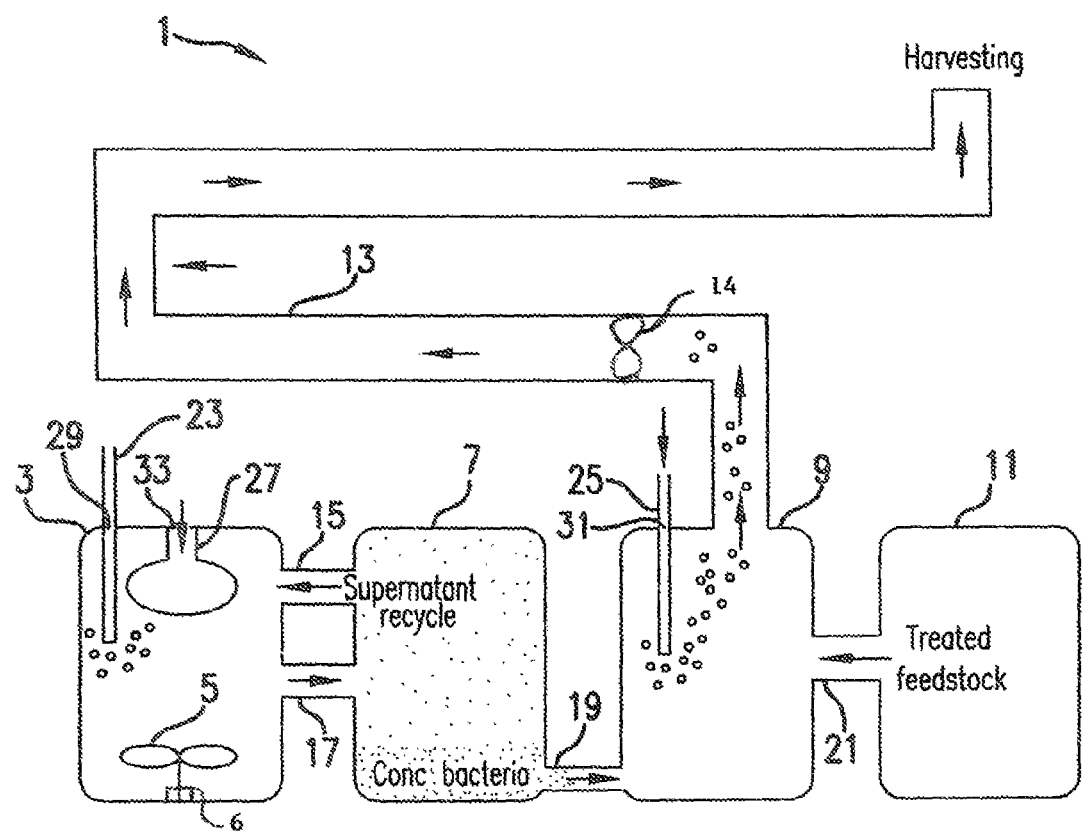

PLUG FLOW REACTOR PROCESS FOR ANAEROBIC CELLULOSIC ETHANOL

RELATED APPLICATIONS

This application is a Continuation-In-Part of U.S. patent application Ser. No. 11/926,213 filed on Oct. 29, 2007, which is incorporated herein by reference.

GOVERNMENTAL INTEREST

The invention described herein may be manufactured, used and licensed by or for the U.S. Government.

FIELD OF THE INVENTION

The present invention is generally related to devices and methods that facilitate sterile growth of one or more anaerobic, ethanol-producing bacteria in the presence of cellulose. The present invention enables the concentration of bacteria, mixing of the bacteria with non-sterile and pretreated biomass, in a manner to facilitate its efficient conversion to ethanol.

BACKGROUND OF THE INVENTION

Biodiesel and ethanol, despite their surging popularity as transportation fuels, barely put a dent in our use of oil. However, that could change because the biggest well in biofuels has yet to be tapped, i.e., lignocellulose, the woody part of a plant and a potentially abundant source of energy.

Lignocellulose is everywhere—wheat, straw, corn husk, prairie grass, discarded rice, hulls of trees. The trick is developing a means to get the energy out of this abundant resource. Right now that's an expensive process, limited to a handful of pilot plants. The race is on to optimize the technology that can produce biofuels from lignocellulose sources more efficiently. Already several companies and government-funded laboratories have engineered enzymes and microorganisms to optimize lignocellulose degradation and help turn it into fuel.

Bacteria may be used to extract energy out of lignocellulose. Certain bacteria have the genetic basis to produce enzymes able to break down lignocellulose and produce ethanol. Even if an organism is able to efficiently produce ethanol from cellulose at high yields and purity, in order to produce ethanol in large volumes, a manufacturing process and a device must be created to grow and manipulate the bacteria as cellulose is being converted to ethanol. For example, it may be beneficial that the bacteria be cultured under sterile conditions in order to maintain a monoculture. Also, it would be beneficial if the bacteria are grown in the presence of cellulose in order to trigger the production of the cellulose enzymes necessary to break down cellulose into its dimeric (cellobiose) or monomeric (glucose) units. The bacteria also need to be concentrated in order to facilitate the most efficient ethanol production.

SUMMARY OF THE INVENTION

Accordingly, it is an object of the present invention to meet the foregoing needs by providing a system or device able to maintain a monoculture of an organism and at the same time activate the production of enzymes in the organism. The increase in the production of enzymes enables the organism to efficiently metabolize a specific substrate. It is preferred that the device of the present invention be used to grow a monoculture of bacteria able to metabolize cellulose and that the bacteria grown in the device be able to produce ethanol from a pretreated feedstock.

One embodiment of the present invention is a bioreactor comprising: (a) a stir tank having a first aperture; (b) a top chamber attached to the interior of the stir tank accessible from the exterior; (c) a mixing tank having a second aperture; (d) a plug flow reactor and a feedstock tank connected to the mixing tank; and (e) a settling tank connected to the stir tank and to the mixing tank. The present invention, further comprises: (a) a first connection means between the stir tank and the settling tank enabling the flow of material from the settling tank to the stir tank; (b) a second connection means between the stir tank and the settling tank enabling the flow of material from the stir tank to the settling tank; (c) a third connection means between the settling tank and the mixing tank enabling the flow of material from the settling tank to the mixing tank; and (d) a fourth connection means between the mixing tank and the feedstock tank enabling the flow of material from the feedstock tank to the mixing tank. It is preferred that the top chamber is made of a semi-permeable membrane. In addition, it is preferred that a first pipe is connected to the first aperture of the stir tank to allow for the intake of gas into the stir tank, and a second pipe is connected to the second aperture of the mixing tank to allow for the intake of gas into the mixing tank. It is also preferred that the stir tank further includes a mixing means, wherein the mixing means is an impeller connected to a variable speed motor. Also, the present invention preferably comprises a screw drive associated with the plug flow reactor to enable the flow of material from the mixing tank through the plug flow reactor.

In a preferred embodiment the top chamber in the stir tank comprises a semi-permeable polymeric membrane capable of containing sterilized solid cellulose materials and permitting the flow of liquid, bacterial cells, and nutrients into and out of the top chamber. The semi-permeable membrane may be comprised of a non-biodegradable polymeric material having a pore size in the range of 1 to 5 microns. In a most preferred embodiment, the semi-permeable membrane is comprised of polytetrafluoroethylene (PTFE) having a pore size of about 5 microns. A first aperture in the stir tank is used to deliver nitrogen gas to the stir tank creating anaerobic conditions for an anaerobic bacterial culture and permitting nitrogen fixation. A second aperture in the mixing tank is preferably used to deliver nitrogen gas to the mixing tank.

DESCRIPTION OF THE DRAWINGS

The FIGURE is a schematic diagram of the system of the present invention.

DETAILED DESCRIPTION OF THE INVENTION

Reference will now be made to preferred embodiments of this invention, examples and variations of which will be obvious from the description of the invention. The current invention relates to devices and methods which facilitate the growth of an organism able to convert cellulose to ethanol. In order to better understand the invention, the following terms have been defined.

The term "cellulose solid" shall mean a type of plant material, which could be derived from any one or more of many different plants, which can be placed inside a semi-permeable membrane.

Bio-Reactor

One embodiment of the present invention is a device, or a bio-reactor as shown in the FIGURE, including at least four tanks 3, 7, 9, 11 and a plug flow reactor 13. These tanks include a stir tank 3, a settling tank 7, a mixing tank 9, and a feedstock tank 11. Each element of the present invention will now be described in greater detail.

Stir Tank

The stir tank 3 of the present invention includes a top chamber 27, one or more connections 15 and 17 to a settling tank 7 and a first aperture 29. A pipe 23 may be connected to the first aperture 29 to allow the flow of gas into the stir tank 3. The top chamber 27 of the stir tank 3 is designed to retain a stock feed, preferably a sterilized cellulose solid, and is made of a semi-permeable membrane. Appropriate semi-permeable membrane materials are well known in the art, and typically are comprised of synthetic polymeric materials of fixed pore sizes. For example, the semi-permeable membrane of the present invention may be comprised of a non-biodegradable polymeric material having a pore size in the range of 1 to 5 microns. In a most preferred embodiment, the semi-permeable membrane is comprised of polytetrafluoroethylene (PTFE) having a pore size of about 5 microns. This membrane is commercially available as WHATMAN TEFLON (PTFE) membrane TE 38. The top chamber 27 is attached to the stir chamber 3 so as to form another aperture 33 on a wall of the stir tank 3 to allow for insertion of a cellulose solid into the top chamber 27. The semi-permeable membrane of the top chamber 27 is able to retain the cellulose solids and yet permit the passage of liquid, bacterial cells and nutrients into and out of the top chamber 27. It is preferable that the stir tank 3 include a mixing means 5 such as an impeller blade on a shaft connected to a motor 6.

Organisms are grown in the stir tank 3 and when the top chamber 27 contains a cellulose solid, the cellulose solids act as a stimulant to enhance the production of certain proteins, such as cellulase enzymes, present in an organism. The stimulation of the production of cellulase enzymes enhances the organism's ability to break down (metabolize) cellulose. Organisms grown in the stir tank may include bacteria, fungus, and yeast. However, it is preferable that bacteria are grown in the device of the present invention. The bacteria may be either anaerobic or aerobic bacteria. It is preferred that an anaerobic bacteria be cultured in the stir tank 3. In order to support the growth of an anaerobic organism, the stir tank 3 of the present invention allows for gas to be pumped into the stir tank 3. The gas may be an inert gas (not oxygen), and is preferably nitrogen. The nitrogen sparge may be added to the stir tank 3 through an aperture 29 on the side of the stir tank 3. A pipe 23 is preferably attached to this aperture 29 through which nitrogen, or any gas other than oxygen, is pumped into the stir tank. For bacteria capable of nitrogen fixation, the presence of nitrogen gas in the device of the present invention can serve as a nitrogen source for growth while continuously purging the tanks of oxygen.

If the device of the present invention is used to grow one or more aerobic bacteria, then oxygen may be pumped into the stir tank 3 to maintain an aerobic environment. It is preferable to grow a sterile monoculture of bacteria in the stir tank 3.

The advantage of this stir tank 3 design is that cells typically produce cellulase enzymes only when grown in the presence of cellulose as their sole source of carbon, and these enzymes are critical for ethanol production. This design permits exposure of the cells to a relatively small amount of cellulose resulting in the enhanced production of cellulase enzymes in these organisms. These activated cells are subsequently mixed with pretreated feedstock to enhance efficient ethanol production.

Settling Tank

Cells and culture medium are pumped from the stir tank 3 to the settling tank 7, which is preferably static, except for inflow and outflow of material. The settling tank 7 permits settling of the one or more organism(s). The settling tank 7 is connected to both the stir tank 3 and the mixing tank 9. The tanks of the present invention are connected to each other by a connection means 15, 17, 19, and 21, including plastic and metal piping, or any other means that allows the flow of material from tank to tank. It is preferable that there is a first 15 and second 17 connection means between the stir tank 3 and the settling tank 7 and a third connection means 19 between the settling tank 7 and the mixing tank 9. Organisms that have been treated with one or more cellulose solid(s) are transferred from the stir tank 3 to the settling tank 7 through the second connection means 17, while a clarified supernatant, a supernatant containing low cell concentration, is returned to the stir tank 3 from the settling tank 7 through a first connection means 15. Also, concentrated cells (the cells that have settled in the settling tank) are pumped from the bottom of the settling tank 7 through a third connection means 19 to a mixing tank 9. The settling tank 7 uses only gravity to settle the cells, and a pump to deliver them to the mixing tank 9.

Mixing Tank

The mixing tank 9 includes a second aperture 31 and is connected to the settling tank 7, a plug flow reactor 13, and a feedstock tank 11. A fourth connection means 21 is used to connect the mixing tank 9 to the feedstock tank 11. Concentrated cells are moved from the settling tank 7 to the inside of mixing tank 9 through third connection means 19, and at the same time, pretreated feedstock is being pumped into the mixing tank 9 from the feedstock tank 11 through fourth connection means 21. This facilitates the exposure of a treated feedstock to a sufficiently high concentration of bacteria to ensure efficient degradation. Since the feedstock will not likely be completely sterile, it is critical to have a means by which to provide a large inoculum of the desired bacterium in the mixing tank 9.

The sum of the flow from the settling tank 7 to the mixing tank 9 and the return from the settling tank 7 to the stir tank 3 will equal the flow from the stir tank 3 to the settling tank 7. It is preferred that the mixing tank 9 is sparged with nitrogen gas to maintain anaerobic conditions and provide nitrogen fixation. Any gas may be pumped into the mixing tank 9 through an aperture 31 on the mixing tank 9 and it is preferred that a pipe 25 is connected to the aperture 31 through which gas may be transferred from a source to the mixing tank 9. The contents of the mixing tank 9 including the concentrated organism and pretreated cellulose are then moved from the mixing tank 9 into the plug flow reactor 13 by a screw drive 14. Residence time is determined by the volumetric flow rate and volume of the plug flow reactor 13, both of which are adjustable, with the flow rate being dependent on pumping rate and the volume of the reactor being dependent on the total number of sections (length) used. At the end of treatment in the plug flow reactor 13, cells, spent cellulose material, ethanol and other byproducts are continuously harvested for downstream processing.

Several features of the plug flow reactor 13 make it desirable for production of cellulosic ethanol. First, it offers the ideal kinetic configuration for a chemical reactor, since it can be operated continuously while providing fine control over residence time; i.e., any material entering the reactor will have to traverse the entire system at approximately the same flow rate prior to harvesting. And since residence time can be adjusted either by flow rate or by varying the length of the reactor pipes, the process can be controlled very precisely. The presence of the internal screw drive aids process control by enabling both the solids and liquids to move through the reactor with similar residence times.

Feedstock Tank

Pretreatment of a feedstock such as solid cellulose material is conducted in the feedstock tank 11. Pretreatment regimes that may occur in the feedstock tank 11 include enzymatic pretreatment, anhydrous ammonia, steam explosion, and acid hydrolysis, all of which are well known in the art. The bacterial organism(s) are continuously grown and settled in settling tank 7 while the feedstock is continuously pretreated in feedstock tank 11, and both are pumped into and mixed in the mixing tank 9 and then the plug flow reactor 13. Capacity is determined by the number or size of the tanks and the diameter of the plug flow reactor.

In order to maintain the desired biological activity, it is possible to autoclave the pre-treated feedstock prior to degradation. However, autoclaving (i.e. high pressure steam treatment) is slow and labor-intensive and requires considerable energy. It would also be possible to use a similar series of tanks at the beginning of the process followed by a second stirred tank reactor in place of the plug flow reactor, although the agitation of the liquid/solid slurry is likely to interfere with the agitation of the stirred tank, as well as making it difficult to load and empty.

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention without departing from the spirit and scope of the invention as defined in the following claims.

What is claimed is:

1. A bioreactor for anaerobic cellulosic ethanol production, comprising:
   (a) a stir tank having a first aperture;
   (b) a top chamber attached to and positioned within the interior of the stir tank, wherein the top chamber is accessible from the exterior of the stir tank and wherein the top chamber comprises a semi-permeable membrane comprised of a polymeric material of a fixed pore size, and wherein the top chamber retains cellulose solids and permits the passage of liquids, bacterial cells and nutrients into and out of the top chamber;
   (c) a mixing tank having a second aperture;
   (d) a settling tank connected to the stir tank and to the mixing tank; and
   (e) a plug flow reactor and a feedstock tank connected to the mixing tank.

2. The bioreactor of claim 1, further comprising:
   (a) a first connection means between the stir tank and the settling tank enabling the flow of material from the settling tank to the stir tank;
   (b) a second connection means between the stir tank and the settling tank enabling the flow of material from the stir tank to the settling tank;
   (c) a third connection means between the settling tank and the mixing tank enabling the flow of material from the settling tank to the mixing tank; and
   (d) a fourth connection means between the mixing tank and the feedstock tank enabling the flow of material from the feedstock tank to the mixing tank.

3. The bioreactor of claim 1, wherein said semi-permeable membrane comprises a non-biodegradable material having a pore size in the range of from 1 to 5 microns.

4. The bioreactor of claim 3, wherein said semi-permeable membrane comprises a polytetrafluoroethylene membrane having a pore size of about 5 microns.

5. The bioreactor of claim 1, wherein a first pipe is connected to the first aperture to allow for the intake of nitrogen gas into the stir tank to produce anaerobic conditions and permit nitrogen fixation in the stir tank.

6. The bioreactor of claim 1, wherein a second pipe is connected to the second aperture to allow for the intake of nitrogen gas into the mixing tank to maintain anaerobic conditions and permit nitrogen fixation in the mixing tank.

7. The bioreactor of claim 1, wherein the stir tank further comprises means for mixing contents of the stir tank.

8. The bioreactor of claim 7, wherein the mixing means is an impeller blade connected to a shaft and driven by a motor.

9. The bioreactor of claim 1, further comprising a screw drive associated with the plug flow reactor to enable the flow of material from the mixing tank through the plug flow reactor.

10. The bioreactor of claim 1, wherein the top chamber contains a feed stock comprising a solid cellulose material.

11. The bioreactor of claim 10, wherein said feed stock comprises a sterilized solid cellulose material.

12. The bioreactor of claim 1, wherein the settling tank contains an anaerobic bacterial culture.

13. The bioreactor of claim 1, wherein said settling tank is adapted to permit gravitational settling of bacterial cells.

14. The bioreactor of claim 1, wherein said feedstock tank is adapted to pretreat a solid cellulose feedstock.

15. The bioreactor of claim 2, wherein said first connection means permits a clarified supernatant containing low bacterial cell concentration to return to the stir tank from the settling tank.

16. The bioreactor of claim 2, wherein said second connection means permits a solution of bacterial cells to flow from the stir tank to the settling tank.

17. The bioreactor of claim 2, wherein said third connection means is connected to the bottom of the settling tank and is adapted to permit concentrated bacterial cells from the bottom of the settling tank to flow into the mixing tank.

18. The bioreactor of claim 2, wherein said fourth connection means permits pretreated feedstock to flow from the feedstock tank to the mixing tank.

19. The bioreactor of claim 2, wherein the sum of the flow from the settling tank to the mixing tank and the flow from the settling tank to the stir tank is equal to the flow from the stir tank to the settling tank.

* * * * *